(12) United States Patent
Berman et al.

(10) Patent No.: US 7,107,839 B1
(45) Date of Patent: Sep. 19, 2006

(54) SYSTEM AND METHOD FOR THE DETECTION OF BALLISTIC IMPACTS AND/OR PENETRATION OF A PRESSURE VESSEL

(75) Inventors: Morris S. Berman, Olney, MD (US); Jan M. Niemiec, New Market, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/953,738

(22) Filed: Sep. 30, 2004

(51) Int. Cl.
*G01P 15/00* (2006.01)

(52) U.S. Cl. .................. 73/489; 73/40.5 A; 73/602

(58) Field of Classification Search .................. 73/488, 73/496, 40.5 R, 40.5 A, 592, 602, 599, 489; 702/39, 170, 171
See application file for complete search history.

(56) References Cited

U.S. PATENT DOCUMENTS

| | | | |
|---|---|---|---|
| 4,176,543 A | 12/1979 | Nolte et al. | |
| 4,462,249 A | 7/1984 | Adams | |
| 5,461,906 A | 10/1995 | Bogle et al. | |
| 5,625,150 A | 4/1997 | Greene et al. | |
| 5,633,809 A * | 5/1997 | Wissenbach et al. | 702/45 |
| 5,708,195 A * | 1/1998 | Kurisu et al. | 73/40.5 R |
| 5,744,700 A | 4/1998 | Carme et al. | |
| 5,974,862 A * | 11/1999 | Lander et al. | 73/40.5 A |
| 6,453,247 B1 * | 9/2002 | Hunaidi | 702/51 |
| 6,561,032 B1 * | 5/2003 | Hunaidi | 73/597 |
| 6,725,705 B1 * | 4/2004 | Huebler et al. | 73/40.5 A |

* cited by examiner

*Primary Examiner*—Hezron Williams
*Assistant Examiner*—Jacques Saint-Surin
(74) *Attorney, Agent, or Firm*—William Randolph

(57) ABSTRACT

A system and method for determining whether leaks exist in a pressure vessel comprises measuring a mechanical response of the pressure vessel using any of an acoustic sensor and a vibration sensor; processing the mechanical response using a digital signal processor system; categorizing the processed mechanical response into events of interest and events not of interest; and determining if any of a ballistic impact and penetration of the pressure vessel has occurred based on the processed mechanical response, wherein the mechanical response comprises any of an acoustic response and a vibration response, wherein the events of interest comprise any of environmental events and ballistic events, wherein the categorizing comprises differentiating the environmental events from the ballistic events, and wherein the events not of interest comprise noise.

21 Claims, 7 Drawing Sheets

SYSTEM AND METHOD FOR THE DETECTION OF BALLISTIC IMPACTS AND/OR PENETRATION OF A PRESSURE VESSEL

GOVERNMENT INTEREST

The invention described herein may be manufactured, used, and/or licensed by or for the United States Government

BACKGROUND OF THE INVENTION

1. Field of the Invention

The invention generally relates to vessel and/or tank inspection and monitoring, and more particularly to detections and characterizations of impacts and leaks in vessels and/or tanks.

2. Description of the Related Art

Pressure vessels used in commercial and military applications are typically filled with fluids including oil, gasoline, and hazardous liquids and gases. Ideally, these pressure vessels are stored in tamper-proof environments. However, the pressure vessels must often be transported. Due to the portable nature of the pressure vessels, the pressure vessels themselves may be subjected to tampering causing leaks to occur and potentially hazardous situations to arise, especially if the enclosed fluid is flammable or toxic. The tampering may or may not be the result of sabotage or other dubious form of tampering. In fact, the tampering may be a result of chemical or mechanical failures of the pressure vessel due to fatigue, rupture, rusting, or other form of breakdown.

Furthermore, given certain military applications and recent threats to civilian infrastructure, the pressure vessels may be subjected to ballistic impacts from ammunition, projectiles, or missiles. In fact, in some situations friendly fire may result in unintended ballistic impacts on the pressure vessels and in some cases the normal operational environment results in impacts on the pressure vessel. However, some of these impacts may not result in penetration of the pressure vessel. Moreover, some of these impacts are mere noise associated with the transportation of the pressure vessels.

For example, if a pressure vessel were to be transported in or as an integral part of an open vehicle, train, or other form of transportation, stones may skip onto the pressure vessel causing an impact on the pressure vessel. However, these impacts are often minimal causing mere surface abrasions on the pressure vessel to appear, but may, nonetheless, alarm those in proximity to the pressure vessel (for example, the driver of the vehicle) that perhaps the pressure vessel has been penetrated or that the impact has potentially damaged the pressure vessel, which may cause failure at some time in the future.

Additionally, a pressure vessel, which contains a hypothermic fluid may cause condensation to form on the outside of the pressure vessel. When viewed, this condensation may cause alarm if it is not known whether the condensation is in fact condensation, or what the source of the condensation is, or whether the condensation is fluid which has leaked from the pressure vessel itself or from a nearby pressure vessel.

Therefore, there is a need for a system and method to monitor pressure vessels, which provide an accurate determination of any leaks or penetrations of the pressure vessel and which differentiate between significant impacts or leaks and mere noise (i.e., insignificant environmental effects on the pressure vessel, such as minimal impacts or condensation).

SUMMARY OF THE INVENTION

In view of the foregoing, an embodiment of the invention provides a method for monitoring a holding structure such as a pressure vessel or tank, wherein the method comprises connecting at least one sensor to the holding structure, wherein the sensor comprises any of an acoustic sensor and a vibration sensor; measuring a mechanical response of the holding structure using the sensor; processing the mechanical response using a digital signal processor system; categorizing the processed mechanical response into events of interest and events not of interest; and determining if any of a ballistic impact and penetration of the holding structure has occurred based on the processed mechanical response.

According to an embodiment of the invention, the mechanical response comprises any of an acoustic response and a vibration response. Also, the events comprise any of environmental events and ballistic events, wherein the categorizing comprises differentiating the environmental events from the ballistic events, and wherein the step of determining comprises assigning acoustic and vibration signatures to different types of penetration. Also, the events not of interest comprise noise and environmental events. Moreover, in the step of connecting, the acoustic sensor comprises any of a microphone and a hydrophone and the vibration sensor comprises any of an accelerometer and a vibrometer. Additionally, the digital signal processor system comprises a program storage device readable by computer, tangibly embodying a program of instructions executable by the computer to perform the categorizing of the processed mechanical response into events of interest and events not of interest.

Another aspect of the invention provides a method for determining whether leaks exist in a pressure vessel, wherein the method comprises measuring a mechanical response of the pressure vessel using any of an acoustic sensor and a vibration sensor; processing the mechanical response using a digital signal processor system; categorizing the processed mechanical response into events of interest and events not of interest; and determining if any of a ballistic impact and penetration of the pressure vessel has occurred based on the processed mechanical response, wherein the mechanical response comprises any of an acoustic response and a vibration response, wherein the events of interest comprise any of environmental events and ballistic events, wherein the categorizing comprises differentiating the environmental events from the ballistic events, and wherein the events not of interest comprise noise.

Additionally, in the step of measuring, the acoustic sensor comprises any of a microphone and a hydrophone and the vibration sensor comprises any of an accelerometer and a vibrometer. Additionally, in the step of processing, the digital signal processor system comprises a program storage device readable by computer, tangibly embodying a program of instructions executable by the computer to perform the categorizing of the processed mechanical response into events of interest and events not of interest.

Another embodiment of the invention comprises a system for monitoring a holding structure, such as a pressure vessel or tank, wherein the system comprises at least one sensor connected to the holding structure, wherein the sensor comprises any of an acoustic sensor and a vibration sensor, and wherein the sensor is operable for measuring a mechanical response of the holding structure; and a digital signal processor system connected to the sensor, wherein the digital signal processor system comprises means for processing the mechanical response, means for categorizing the processed mechanical response into events of interest and events not of interest, and means for determining if any of a ballistic impact and penetration of the holding structure has occurred based on the processed mechanical response, wherein the mechanical response comprises any of an acoustic response and a vibration response, wherein the events of interest comprise any of environmental events and ballistic events, and wherein the digital signal processor system further comprises means for differentiating the environmental events from the ballistic events.

The system further comprises a radio transmitter connected to the sensor and a radio receiver connected to the digital signal processor system. Additionally, the digital signal processor system further comprises means for assigning acoustic signatures to different types of penetration, wherein the events not of interest comprise noise, and wherein the acoustic sensor comprises any of a microphone and a hydrophone and the vibration sensor comprises any of an accelerometer and a vibrometer. Furthermore, the digital signal processor system comprises a radio transmitter operable for communicating the events of interest to a central dispatch location.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which.

DETAILED DESCRIPTION OF PREFERRED EMBODIMENTS OF THE INVENTION

Figure 1A:
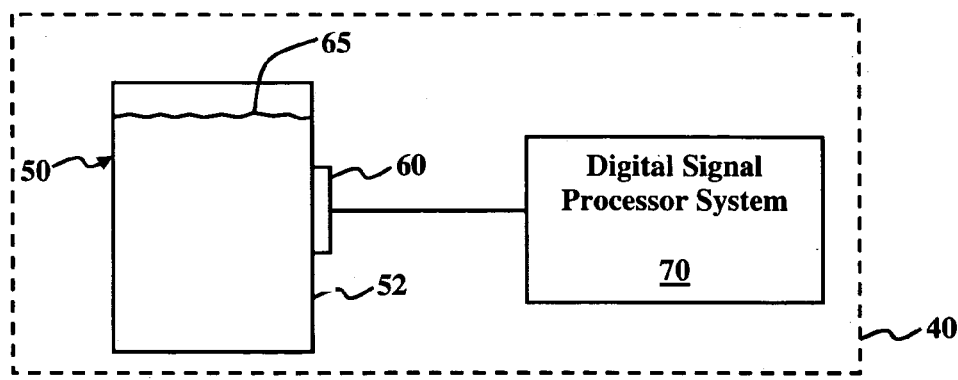
FIG. 1(a) is a system diagram according to an embodiment of the invention.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As previously mentioned, there remains a need for a system and method to monitor pressure vessels, which provide an accurate determination of any leaks or penetrations of the pressure vessel and which differentiate between significant impacts or leaks and mere noise (i.e., insignificant environmental effects on the pressure vessel, such as minimal impacts or condensation). Referring now to the drawings, and more particularly to FIGS. 1 through 8, there are shown preferred embodiments of the invention.

FIGS. 1(a) through 5(c) illustrate a system 40 for monitoring a holding structure, preferably embodied as a pressure vessel (or tank) 50 filled with a product 65 (such as a gas or fluid which may include hazardous materials) according to the invention, wherein the system 40 comprises at least one sensor 60 connected to the pressure vessel 50. As shown in FIG. 1(a), the sensor 60 is shown attached on the outer surface 52 of the pressure vessel 50, while in FIG. 1(b), the sensor 60 is shown attached on the inner surface 53 of the pressure vessel 50, while in FIG. 1(c) one sensor 60 is shown on the interior of the pressure vessel 50 and one on the exterior 60 of the pressure vessel 50. As shown in FIG. 2(a), the sensor 60 comprises an acoustic sensor 61 (such as a microphone or hydrophone, for example) and a vibration sensor 62 (such as an accelerometer or vibrometer, for example). Moreover, any well-known acoustic and vibration sensors 61, 62 known to those skilled in the art may be used. Additionally, the sensor 60 is operable for measuring a mechanical response (acoustic and vibration response) of the pressure vessel 50.

The system 40 further comprises a digital signal processor system 70 connected to the sensor 60, wherein the digital signal processor system 70 comprises means for processing the mechanical response, means for categorizing the processed mechanical response into events of interest and events not of interest, and means for determining if any of a ballistic impact and penetration of the pressure vessel has occurred based on the processed mechanical response, wherein the mechanical response comprises any of an acoustic response and a vibration response, wherein the events of interest comprise any of environmental events and ballistic events, wherein the digital signal processor system 70 further comprises means for differentiating the environmental events from the ballistic events. Moreover, the digital signal processor system 70 may incorporate computers, calculators, generators, transmitters, receivers, radios, comparators, detectors, decoders, and other data generation, consolidation, and calculation devices arranged to perform the functions described above. Furthermore, those skilled in the art will readily understand implementing such an arrangement to perform the functions described above.

Figure 2A:
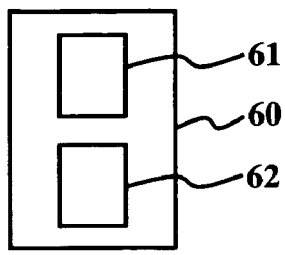
FIG. 2(a) is an isolated view of the sensor of FIGS. 1(a) and 1(b) according to an embodiment of the invention.
Figure 2B:
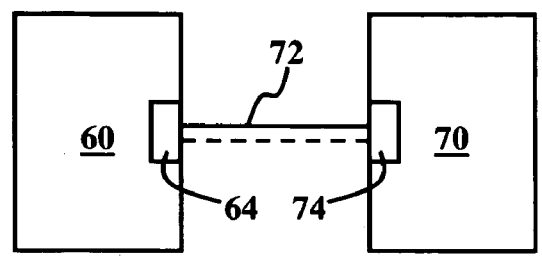
FIG. 2(b) is an isolated view of the connection between the sensor and digital signal processor system of FIGS. 1(a) and 1(b)

Additionally, the digital signal processor system 70 further comprises means for assigning signatures to different types of penetration, wherein the events not of interest comprise noise. Furthermore, the sensor 60 may be connected to the digital signal processor system 70 by wires 72, or the connection may be wireless (indicated by the dashed line in FIG. 2(b)) whereby the sensor 60 includes a radio transmitter 64 and the digital signal processor system 70 includes a radio receiver 74 for wireless communication therebetween, as illustrated in FIG. 2(b).

For example, a penetration event would result in the flow of a product 65 such as a fluid from the pressure vessel 50 that would result in a unique signature on the sensor 60 enabling the digital signal processor system 70 to determine if a penetration has actually occurred or if the pressure vessel 50 has been damaged to the extent which may cause a future penetration to occur. Preferably, the system 40 is programmed with identifying signatures associated with different types of penetration. These identifying signatures are preferably programmed as levels of frequency associated with types of signals which may be sensed by the sensor 60.

Figure 1B:
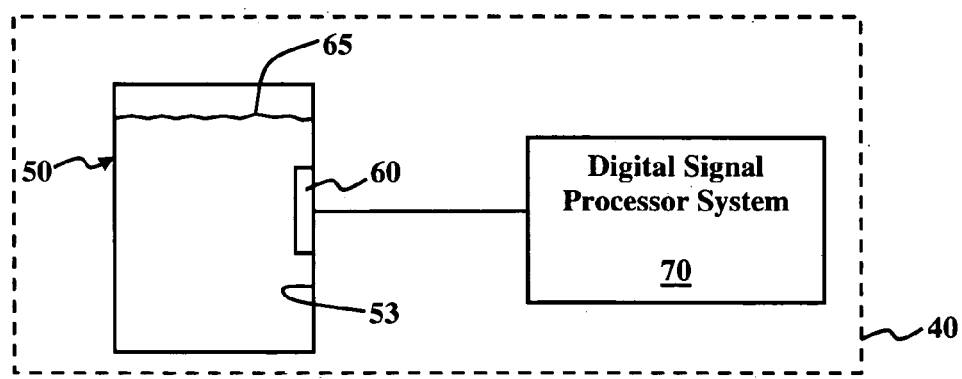
FIG. 1(b) is an alternate system diagram according to an embodiment of the invention.
Figure 1C:
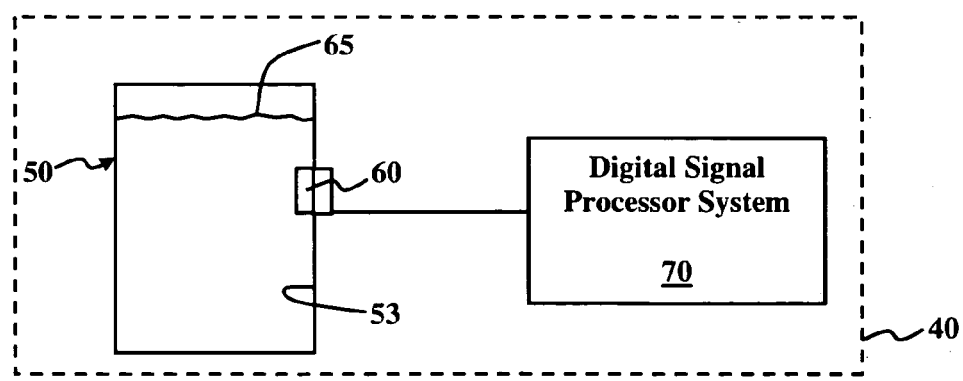
FIG. 1 (c) is another alternate system diagram according to an embodiment of the invention.
Figure 3:
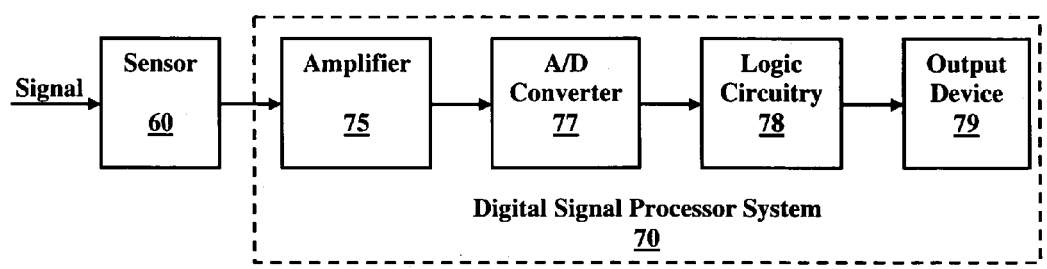
FIG. 3 is a system block diagram according to an embodiment of the invention.

FIG. 3 illustrates a general block diagram incorporating the system 40 of FIGS. 1(a) and 1(b). As shown in FIG. 3, an input signal is sensed by a sensor 60, which may be embodied as a sensor-transducer, which generally converts an acoustic and/or vibration signal to an analog electrical signal. This analog signal is then sent to the digital signal processor system 70, which includes an amplifier 75 connected to an analog-to-digital (A/D) converter 77, which is further connected to logic circuitry (such as an integrated circuit) 78, which is then connected to an output device 79. The amplifier 75, which receives the analog signal, amplifies, filters, and generally conditions the analog signal. Next, the conditioned analog signal is sent to the A/D converter 77, which converts the analog signal to a digital signal. The logic circuitry 78 then converts the digital signal to a format capable of being interpreted by the output device 79. For example, the format may include a frequency domain format such as a fast Fourier transform (FFT) logic format. Moreover, as shown in FIG. 5(c), the output device 79 may include a monitor 38, printer 39 used for displaying the results, or other output device such as a radio transmitter device 41 used for wireless transmission of the results to a central dispatch location (not shown).

Figure 4:
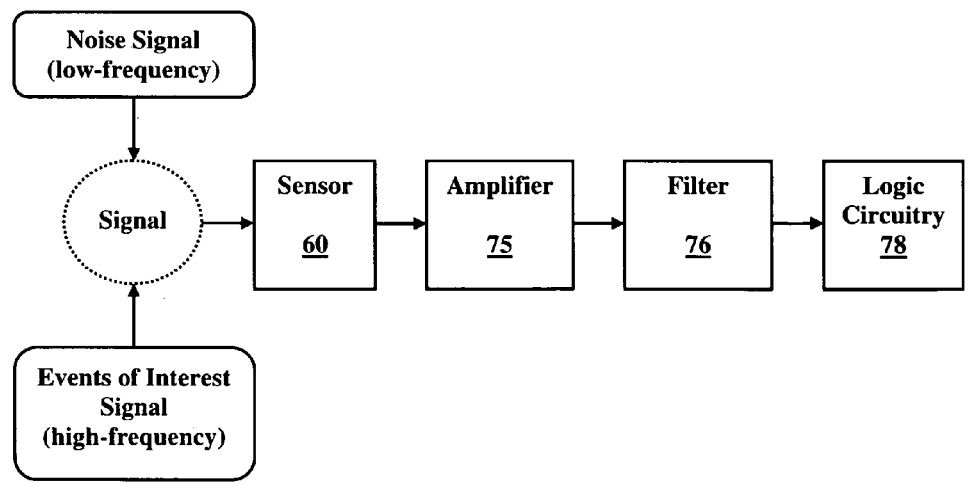
FIG. 4 is a first alternate system block diagram according to an embodiment of the invention.

FIG. 4 illustrates an example of the manner in which the invention separates events of interest from events not of interest (i.e., noise). As shown in FIG. 4, an input signal is sensed by the sensor 60. This input signal includes signals which are significant (i.e., relate to the product 65 to be measured) as well as insignificant noise. According to the invention, the sensor 60 and digital signal processor system 70 are programmed to associate a first frequency with events of interest and a second frequency, preferably a low-frequency signal, with events not of interest (i.e., noise). Thus, if the sensor 60 measures a high-frequency signal, then the digital signal processor system 70 will characterize this high frequency signal as events of interest, whereas low-frequency signals are characterized as events not of interest (i.e., noise).

The digital signal processor system 70 is able to characterize the signals in this manner by using an amplifier 75 in combination with a filter 76 connected to logic circuitry 78, such as an integrated circuit. Thus, after passing through the sensor 60, the combined signal (combined significant and noise signal) is amplified in the amplifier 75, which then sends the signal to the filter 76. Here, only high-frequency signals, which are predetermined to be over the threshold established by a predetermined level for the low-frequency signal, are passed on to the logic circuitry 78. In other words, the low-frequency signals associated with noise or other events not of interest are filtered out. Thereafter, the logic circuitry 78 provides the filtered event of interest signal.

Figure 5A:
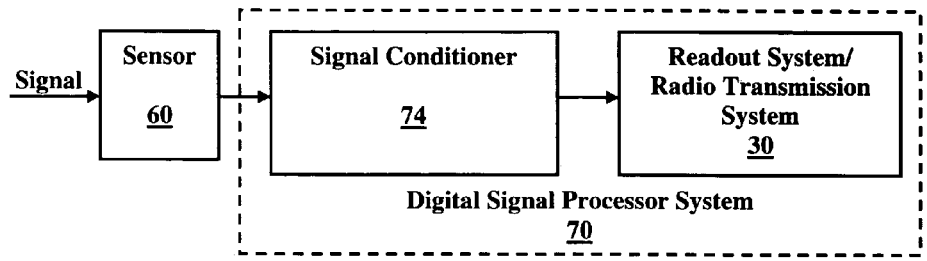
FIG. 5(a) is a second alternate system block diagram according to an embodiment of the invention.
Figure 5B:
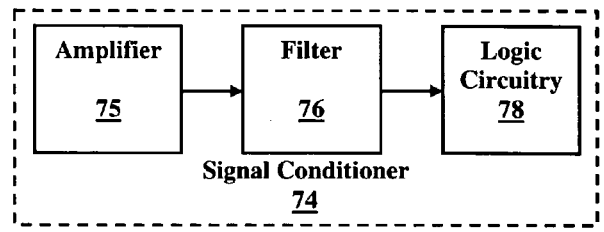
FIG. 5(b) is an isolated system block diagram of the signal conditioner of FIG. 5(a) according to an embodiment of the invention.
Figure 5C:
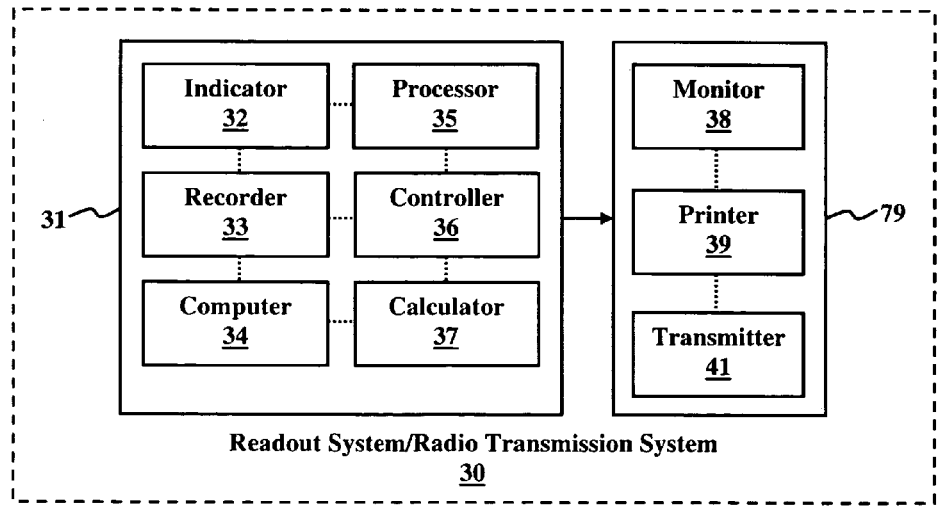
FIG. 5(c) is an isolated system block diagram of the readout system/radio transmission system of FIG. 5(a) according to an embodiment of the invention.

FIGS. 5(a) through 5(c) further illustrate an example of an alternate configuration of the manner in which the invention separates events of interest from events not of interest (i.e., noise). As shown in FIG. 5(a), the signal is input into the sensor 60, which is then sent to the digital signal processor system 70, which generally includes a signal conditioner 74 for receiving the signal, transforming it, and sending it to a readout system/radio transmission system 30. As shown in FIG. 5(b), the signal conditioner 74 generally comprises an amplifier 75 for amplifying the signal, a filter 76 for filtering different levels of frequencies associated with the signal, and logic circuitry 78 for processing the filtered signals. As shown in FIG. 5(c), the readout system/radio transmission system 30 generally includes a series of processing devices 31, which may be used separately or in conjunction with one another, wherein the processing devices 31 may include an indicator 32, a recorder 33, a computer 34, a processor 35, a controller 36, and a calculator 37. The signals from the logic circuitry 78 are sent to the processing devices 31, which then send the signals in a readable format to an output device 79 such as a monitor 38, printer 39, or a radio transmitter device 41. According to an embodiment of the invention, the radio transmitter device 41 is operable for alerting a central dispatch location (not shown) of a critical event relating to an event of interest.

Figure 6:
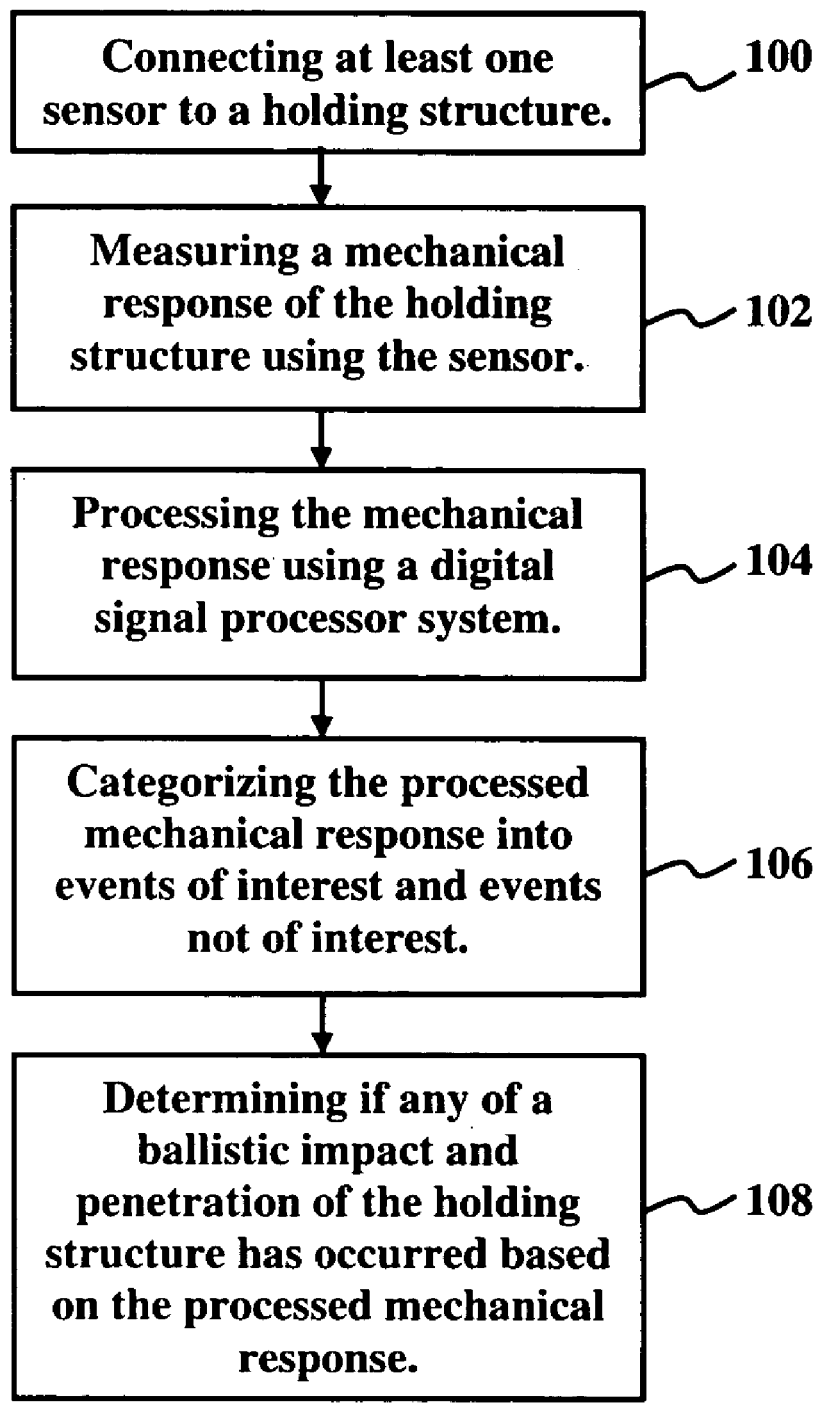
FIG. 6 is a flow diagram illustrating a method according to an embodiment of the invention.

The flow diagram of FIG. 6, which includes descriptions which refer to components provided in FIGS. 1 through 5(c), illustrates a method for monitoring a holding structure, preferably embodied as a pressure vessel (or tank) 50, wherein the method comprises connecting (100) at least one sensor 60 to the holding structure 50, wherein the sensor 60 comprises an acoustic sensor 61 and a vibration sensor 62. Next, the method comprises measuring (102) a mechanical response of the holding structure 50 using the sensor 60, processing (104) the mechanical response using a digital signal processor system 70, categorizing (106) the processed mechanical response into events of interest and events not of interest, and determining (108) if any of a ballistic impact, leak and penetration of the holding structure 50 has occurred based on the processed mechanical response.

According to the invention, the mechanical response comprises any of an acoustic response and a vibration response. Additionally, the events comprise any of environmental events and ballistic events. Also, the step of categorizing (106) comprises differentiating the environmental events from the ballistic events, and the step of determining (108) comprises assigning acoustic signatures to different types of penetration. Furthermore, the events not of interest comprise noise and environmental events.

Moreover, associated with the step of connecting (100), the acoustic sensor 61 comprises any of a microphone and a hydrophone, and the vibration sensor 62 comprises any of an accelerometer and a vibrometer. Additionally, associated with the step of processing (104), the digital signal processor system 70 comprises a program storage device readable by computer, tangibly embodying a program of instructions executable by the computer to perform the categorizing (106) of the processed mechanical response into events of interest and events not of interest, which is further shown in FIG. 7.

Figure 7:
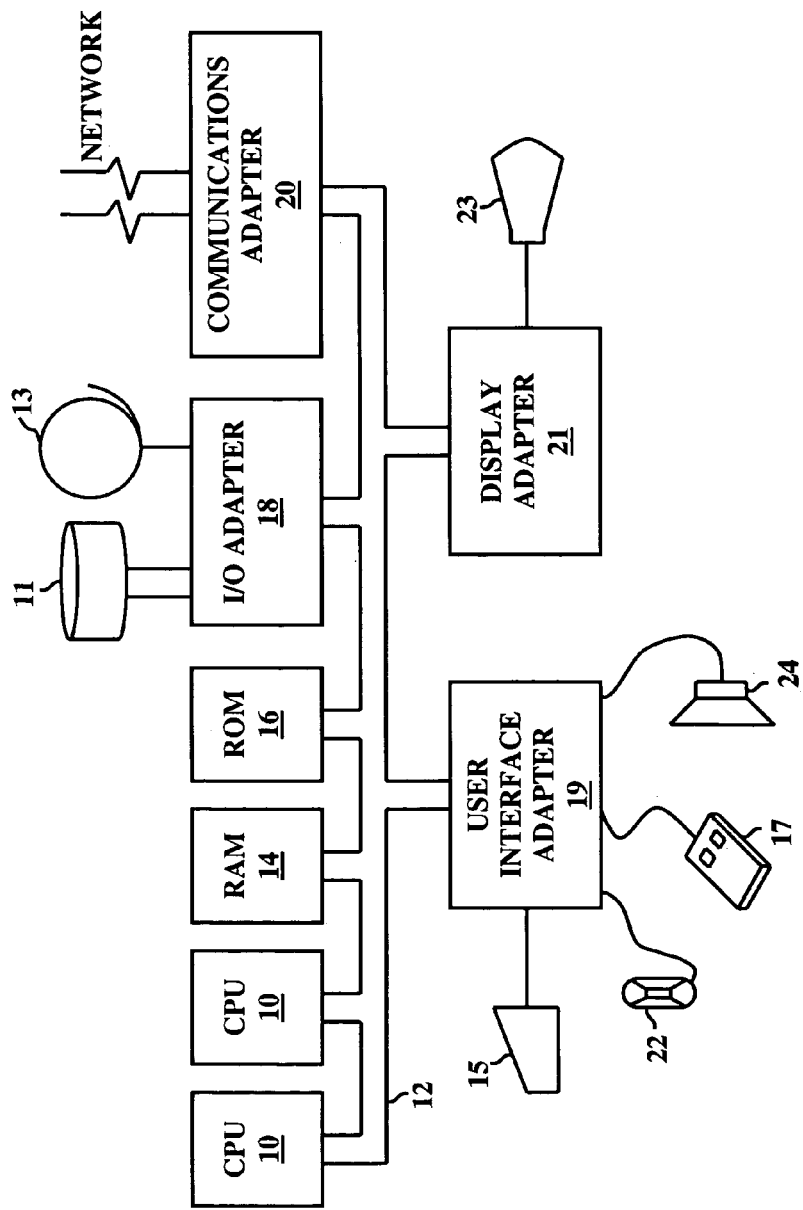
FIG. 7 is a computer systems diagram according to an embodiment of the invention.

For example, a representative hardware environment for practicing the invention is depicted in FIG. 7, which illustrates a typical hardware configuration of an information handling/computer system, used in conjunction with the digital signal processor system 70 in accordance with the invention, having at least one processor or central processing unit (CPU) 10. The CPUs 10 are interconnected via system bus 12 to random access memory (RAM) 14, read-only memory (ROM) 16, an input/output (I/O) adapter 18 for connecting peripheral devices, such as disk units 11 and tape drives 13, to bus 12, user interface adapter 19 for connecting keyboard 15, mouse 17, speaker 24, microphone 22, and/or other user interface devices such as a touch screen device (not shown) to bus 12, communication adapter 20 for connecting the information handling system to a data processing network, and display adapter 21 for connecting bus 12 to display device 23. A program storage device readable by the disk or tape units is used to load the instructions, which operate the invention, which is loaded onto the computer system.

Figure 8:
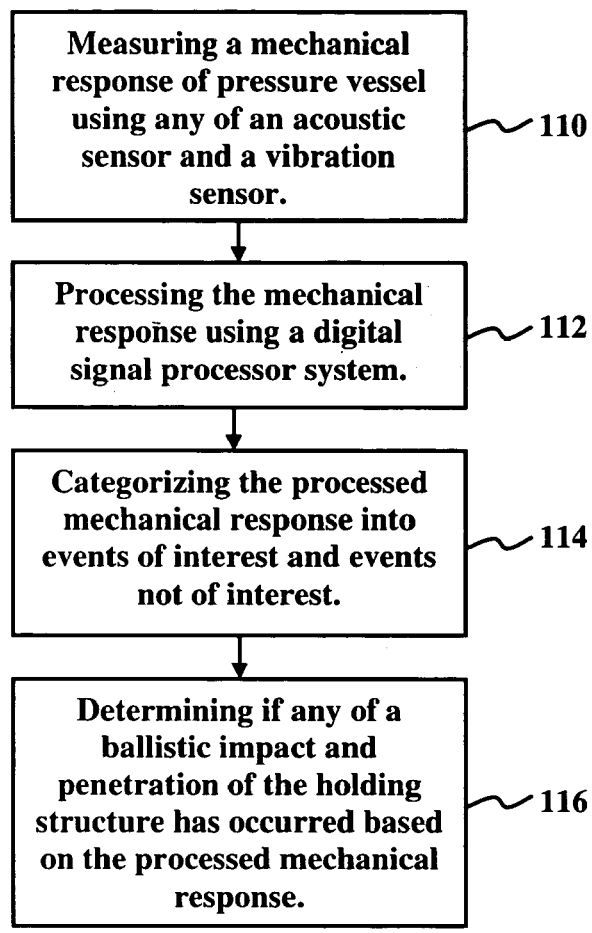
FIG. 8 is an alternate flow diagram illustrating a preferred method according to an embodiment of the invention.

FIG. 8 illustrates a flow diagram illustrating another aspect of the invention, wherein FIG. 8 illustrates a method for determining whether leaks exist in a pressure vessel 50, wherein the method comprises measuring (110) a mechanical response of the pressure vessel 50 using any of an acoustic sensor 61 and a vibration sensor 62, processing (112) the mechanical response using a digital signal processor system 70, categorizing (114) the processed mechanical response into events of interest and events not of interest, and determining (116) if any of a ballistic impact and penetration of the pressure vessel 50 has occurred based on the processed mechanical response.

Generally, the invention provides a system and method for the automatic detection of ballistic impacts to, and penetrations of, a pressure vessel 50. Such detection is particularly useful for the identification and notification of imminent threats associated with a potentially exposed hazardous material. The invention utilizes a combination of acoustic and vibration sensors 61, 62 to measure the mechanical response of a pressure vessel 50. A digital signal processor system 70 is used to implement a computer-readable methodology that differentiates noise and environmental events from events of interest (or events of significance) such as leaks and ballistic impacts.

As such, the digital signal processor system 70 uses the input from the sensor 60, which may be embodied as a single sensor format or a multi-sensor format, to separate the event of interest from noise. The system 40 does not rely on pressure changes to sense the impact or penetration. This non-reliance on pressure changes is advantageous because the system 40 monitors large pressure vessels 50 (e.g., on the order of 140,000 lbs water equiv.) that may contain hazardous materials. If even a small quantity (compared to the total cargo) of the hazardous material leaks, it potentially could result in a substantially hazardous and dangerous environment to people who may be near the pressure vessels 50, yet may result in a minimal pressure change inside the pressure vessel 50.

Rather, the system 40 uses mechanical responses (acoustic and vibration responses) of the pressure vessel 50 as measured by the sensor 60. Additionally, the embodiments of the invention are easily implementable with minimal modification to the pressure vessel 50 being monitored, as the system 40 is portable. The digital signal processor system 70 is configured to enable the system 40 to monitor a variety of characteristics of the pressure vessel 50 that manifest themselves in structural vibration. Specifically, the digital signal processor system 70 may include monitoring of evidences of tampering and surreptitious extraction of contents of the pressure vessel 50, as well as health monitoring of the pressure vessel 50. If the pressure vessel 50 is integral to a mobile platform (not shown), then the health monitoring and environmental monitoring of the mobile platform would also be included in the overall monitoring performed by the digital processor system 70. For example, if the mobile platform is a vehicle such as a truck, then the number of hitch/unhitch occurrences for maintenance scheduling or other purposes could be monitored. If the mobile platform is a train, then the coupling force of the train could be monitored. If the mobile platform includes any type of rotating machinery, then the bearing noise could be monitored.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the invention has been described in terms of preferred embodiments, those skilled in the art will recognize that the embodiments of the invention can be practiced with modification within the spirit and scope of the appended claims.

What is claimed is:

1. A method for monitoring a vessel for ballistic impacts and penetration of the vessel, comprising:
    connecting a sensor to the vessel, wherein the sensor is selected from the group of an acoustic sensor and a vibration sensor;
    measuring any of an acoustic mechanical response and a vibration mechanical response of the vessel using the sensor;
    processing the measured mechanical response using a digital signal processor means;
    categorizing the processed mechanical response into events of interest and events not of interest, wherein the digital signal processor means comprises a program storage device readable by a computer, tangibly embodying a program of instructions executable by the computer to perform categorizing of the processed mechanical response into events of interest and events not of interest, wherein the events of interest comprise any of environmental events and ballistic events, mid the categorizing step further comprises differentiating environmental events from ballistic events; and
    determining if any of a ballistic impact and a penetration of the vessel has occurred based on the processed mechanical response.

2. The method of claim 1, wherein the events not of interest comprise noise.

3. The method of claim 1, wherein in the connecting step, the acoustic sensor comprises a hydrophone and the vibration sensor comprises an accelerometer.

4. The method of claim 1, wherein in the connecting step, the vessel comprises a pressure vessel.

5. The method of claim 1, wherein the processing step comprises assigning processed mechanical responses for different types of known ballistic penetrations and leakage events of the vessel, and the categorizing step comprises comparing a processed mechanical response with the assigned processed mechanical responses for the different types of known penetrations and leakage events, to differentiate environmental events from ballistic events.

6. The method of claim 5 wherein the measured mechanical signal comprises an analog signal, and wherein the digital signal processor means receives the analog signal, converts the analog signal to a digital signal, amplifies and filters the analog signal, converts the analog signal to a digital signal, and converts the digital signal to a format capable of being interpreted by a logic and output means.

7. The method of claim 1 wherein the measured mechanical signal comprises an analog signal, and wherein the digital signal processor means receives the analog signal, converts the analog signal to a digital signal, amplifies and filters the analog signal, converts the analog signal to a digital signal, and converts the digital signal to a format capable of being interpreted by a logic means and a output means.

8. The method of claim 7 wherein the logic means compares the digital signal with digital signals for different types of penetration of the vessel to determine if any of a ballistic impact or penetration of the vessel has occurred.

9. The method of claim 1 wherein the sensor comprises an acoustic sensor.

10. The method of claim 1 wherein the sensor comprises a vibration sensor.

11. The method of claim 1 wherein the sensor comprises a vibration sensor and an acoustic sensor positioned together and attached to the vessel.

12. A method for monitoring a holding structure for ballistic impacts or penetration of the holding structure comprising:
   connecting an acoustic sensor and a vibration sensor to the holding structure;
   measuring any of an acoustic mechanical response and a vibration mechanical response of the holding structure with the sensors;
   processing the mechanical responses using a digital signal processor system, wherein the digital signal processor assigns frequency signals for different types of known ballistic impacts and penetrations of the holding structure;
   categorizing the frequency signal of the processed mechanical responses of interest into any of environmental events and ballistic events by comparing the processed mechanical response signal of interest with the assigned frequency signals for different types of known penetrations, to categorize and distinguish different environmental events from ballistic events; and
   determining if any of a ballistic impact or a penetration of the container has occurred based on the processed mechanical response signal.

13. A method for monitoring a holding structure for ballistic impacts and penetration of the holding structure comprising:
   connecting a sensor to the holding structure, wherein the sensor is selected from the group of an acoustic sensor and a vibration sensor;
   measuring any of an acoustic and a vibration mechanical response signal of the holding structure using the sensor;
   processing the mechanical response signal using a digital signal processor system, wherein the mechanical response signal is converted to a digital signal where frequency signals less than a predetermined threshold frequency are considered an event not of interest and frequency signals equal to or greater than the predetermined threshold frequency are considered an event of interest;
   categorizing the processed mechanical response signal of interest, wherein the digital signal processor system comprises a program storage device readable by computer, tangibly embodying a program of instructions executable by the computer to perform the categorizing of the processed mechanical response signal of interest into any of environmental events and ballistic events by comparing the processed mechanical response signal of interest with known signals of different types of penetration for the holding structure to categorize and distinguish different environmental events from ballistic events; and
   determining if any of a ballistic impact and a penetration of the holding structure has occurred based on the processed mechanical response signal.

14. A system for monitoring a vessel for ballistic impacts and penetration of the vessel, comprising:
   at least one sensor connected to the vessel, wherein each sensor is selected from the group of an acoustic sensor and a vibration sensor; and wherein each sensor is operable for measuring mechanical responses of the vessel;
   a digital signal processor system connected to the sensors, the digital signal processor system comprising:
   means for processing the mechanical responses wherein the mechanical responses comprise any of an acoustic response and a vibration response and wherein the digital signal processor system further comprises means for assigning acoustic and vibration signatures to different types of impact or penetration of the vessel;
   means for categorizing a processed mechanical response into events of interest and events not of interest by comparing the processed mechanical response with the assigned acoustic and vibration signatures, wherein events of interest comprise any of environmental events and ballistic events; and
   means for determining if any of a ballistic impact and a penetration of the vessel has occurred based on the processed mechanical response.

15. The system of claim 14, wherein the events not of interest comprise noise.

16. The system of claim 14, wherein the acoustic sensor and the vibration sensor are positioned together and attached to the vessel.

17. The system of claim 14, wherein the vessel comprises a pressure vessel.

18. The system of claim 14, further comprising:
   a radio transmitter connected to the sensor; and
   a radio receiver connected to the digital signal processor system.

19. The system of claim 14, wherein said digital signal processor system further comprises a radio transmitter operable for communicating the d events of interest to a central dispatch location.

20. The system of claim 14, wherein the measured mechanical response comprises an analog signal, and wherein the digital signal processor means receives the analog signal, amplifies and filters the analog signal, converts the analog signal to a digital signal, and converts the digital signal to a format capable of being interpreted by a logic means and an output means.

21. The method of claim 20 wherein the logic means compares the digital signed with digital signals for different types of known ballistic impacts or penetrations of the vessel to determine if any of a ballistic impact or a penetration of the vessel has occurred.

* * * * *